United States Patent
Tethrake et al.

(10) Patent No.: US 7,268,684 B2
(45) Date of Patent: Sep. 11, 2007

(54) WORKSTATION RFID READER FOR SURGICAL INSTRUMENTS AND SURGICAL INSTRUMENT TRAYS AND METHODS OF USING SAME

(75) Inventors: Steven M. Tethrake, North Webster, IN (US); Robert Varner, Germantown, TN (US); Jeffrey H. Nycz, Collierville, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 92 days.

(21) Appl. No.: 11/006,750

(22) Filed: Dec. 8, 2004

(65) Prior Publication Data

US 2006/0119481 A1    Jun. 8, 2006

(51) Int. Cl.
G08B 13/14    (2006.01)

(52) U.S. Cl. .............. 340/572.1; 340/572.4; 340/539.12

(58) Field of Classification Search ........ 340/572.1, 340/572.4, 573.1, 539.12, 539.32, 10.1, 10.3, 340/10.4, 10.41, 10.42, 10.31; 604/362; 606/1
See application file for complete search history.

(56) References Cited

U.S. PATENT DOCUMENTS

| | | | |
|---|---|---|---|
| 4,075,632 A | 2/1978 | Baldwin et al. | |
| 4,360,801 A | 11/1982 | Duhame | |
| 4,390,880 A | 6/1983 | Henoch | |
| 4,688,026 A | 8/1987 | Scribner et al. | |
| 4,739,328 A | 4/1988 | Koelle et al. | |
| 5,030,807 A | 7/1991 | Landt et al. | |
| 5,621,199 A | 4/1997 | Calari et al. | |
| 5,923,001 A | 7/1999 | Morris et al. | |
| 5,963,134 A | 10/1999 | Bowers et al. | |
| 6,084,512 A * | 7/2000 | Elberty et al. | 340/572.1 |
| 6,158,437 A | 12/2000 | Vagley | |
| 6,164,738 A | 12/2000 | Dane et al. | |
| 6,318,636 B1 | 11/2001 | Reynolds et al. | |
| 6,366,206 B1 * | 4/2002 | Ishikawa et al. | 340/573.1 |
| 6,405,863 B1 | 6/2002 | Dhindsa | |

(Continued)

OTHER PUBLICATIONS

Presentation by Innovision Research and Technology, PLC at the "RFID in Healthcare" conference in Washington, DC. on Dec. 2 and 3, 2003.

(Continued)

Primary Examiner—Van T. Trieu
(74) Attorney, Agent, or Firm—Goodwin Procter LLP

(57) ABSTRACT

A radio frequency identification (RFID) workstation reader for RFID-enabled surgical instruments and surgical instrument trays and a method of using a RFID workstation reader to read RFID-enabled surgical instruments and surgical instrument trays. The method, apparatus, and system enable individual instruments or a surgical instrument tray containing several surgical instruments to be quickly and efficiently inventoried and tracked. An instrument or instrument tray is placed on the workstation reader. An RF field generated by a plurality of antennae, causes RFID tags embedded in or attached to the instrument or instrument tray to emit a signal containing item specific identification information stored in the tags. The information is received by a control circuit and passed to a computer for data analysis. A status LED is illuminated on the workstation reader based on the results of the data analysis. The method, apparatus, and system can track, inspect, and verify inbound and outbound surgical instrument kits, and help to assess the surgical instruments' and trays' duty life cycle usage.

19 Claims, 4 Drawing Sheets

U.S. PATENT DOCUMENTS

| | | |
|---|---|---|
| 6,415,978 B1 | 7/2002 | McAllister |
| 6,426,041 B1 | 7/2002 | Smith |
| 6,429,776 B1 | 8/2002 | Alicot et al. |
| 6,480,101 B1 | 11/2002 | Kelly et al. |
| 6,523,752 B2 | 2/2003 | Nishitani et al. |
| 6,646,241 B1 | 11/2003 | Varma et al. |
| 6,669,089 B2 | 12/2003 | Cybulski et al. |
| 6,777,623 B2 | 8/2004 | Ballard |
| 6,825,766 B2 | 11/2004 | Hewitt et al. |
| 6,853,303 B2 | 2/2005 | Chen et al. |
| 6,861,954 B2 | 3/2005 | Levin |
| 6,866,147 B2 | 3/2005 | Barwick |
| 6,967,563 B2 * | 11/2005 | Bormaster ............... 340/10.31 |
| 6,967,577 B2 * | 11/2005 | Taylor et al. ............ 340/572.1 |
| 2002/0032435 A1 | 3/2002 | Levin |
| 2002/0063622 A1 | 5/2002 | Armstrong et al. |
| 2002/0105424 A1 | 8/2002 | Alicot et al. |
| 2002/0143320 A1 | 10/2002 | Levin |
| 2002/0188259 A1 | 12/2002 | Hickle et al. |
| 2003/0164401 A1 | 9/2003 | Andreasson et al. |
| 2003/0174099 A1 | 9/2003 | Bauer et al. |
| 2003/0189094 A1 | 10/2003 | Trabitz |
| 2003/0196837 A1 | 10/2003 | Ballard |
| 2004/0008123 A1 | 1/2004 | Carrender et al. |
| 2004/0022227 A1 | 2/2004 | Lynch et al. |
| 2004/0031626 A1 | 2/2004 | Morris et al. |
| 2004/0069851 A1 | 4/2004 | Grunes et al. |
| 2004/0100384 A1 | 5/2004 | Chen et al. |
| 2004/0160233 A1 | 8/2004 | Forster |
| 2004/0174244 A1 | 9/2004 | Eidemiller |
| 2004/0174261 A1 | 9/2004 | Volpi et al. |
| 2004/0220602 A1 | 11/2004 | Deng et al. |
| 2004/0220860 A1 | 11/2004 | Persky et al. |
| 2004/0250819 A1 | 12/2004 | Blair et al. |
| 2004/0267297 A1 | 12/2004 | Malackowski |
| 2005/0003757 A1 | 1/2005 | Anderson |
| 2005/0012617 A1 | 1/2005 | DiSilvestro et al. |

OTHER PUBLICATIONS (http://rfidjournal.com/article/view/112) RFID Journal, Can RFID Cure Healthcare's Ills?, Nov. 12, 2002.

(http://usatoday.printthis.clickability.com/pt/cpt?action=cpt&expire=&urlID=8067862&fb=...) Svensson, Peter "Conductive ink advances electronics," USATODAY.com—(New York) pp. 1-3.

(http://www.eetimes.com/showPressRelease.jhtml?articleID=57907) EE Times (www,eetimes.com) "T-Ink™ Unique Conductive Ink Technology to Be Featured" Feb. 14, 2003, pp. 1-2.

(http://americanprinter.com/microsites/magazinearticle.asp?mode=print&magazinearticleid...) American Printer (www.americanprinter.com) "Tracking RFID Progress" Jan. 1, 2004, pp. 1-3.

(http://pffc-online.com/microsites/newsarticle.asp?mode=print&newsarticleid=2708965&re) Byrd-Thompson, Nsenga, (PFFC) Paper Film & Foil Converter (www.pffc-online.com), "RFID and Conductive Inks: What You Need To Know" pp. 1-3.

* cited by examiner

WORKSTATION RFID READER FOR SURGICAL INSTRUMENTS AND SURGICAL INSTRUMENT TRAYS AND METHODS OF USING SAME

FIELD OF THE INVENTION

The invention generally relates to an apparatus and method for implementing radio frequency identification techniques, and more particularly to an apparatus and method for wirelessly inventorying surgical instruments and surgical instrument trays in order to facilitate tracking and inventory management of surgical instruments and surgical instrument trays over their useful life cycle.

BACKGROUND OF THE INVENTION AND DESCRIPTION OF RELATED ART

Surgical instrument storage and sterilization systems are known. These systems, known as surgical instrument trays or surgical instrument kits, typically consist of metal or plastic trays that hold a variety of general purpose and/or procedure specific surgical instruments such as forceps, scissors, clamps, retractors, scalpels, etc. These trays are brought into the operating room (OR) when preparing for surgery, and also are used as a means to organize, transport and store surgical instruments in a medical facility.

Due to advances in medical technology that have increased the number of surgical instruments now in use and due to the constant pressure in the health care industry to reduce operating costs, it has become necessary to manage and track these instruments more quickly and efficiently. One advancement towards this end has been the creation of surgical instrument trays that employ various techniques for controlling the arrangement of instruments on the tray so that any missing instruments can be identified quickly. Once such method is disclosed in U.S. Pat. No. 6,158,437, which uses a combination of instrument identifying indicia including a plurality of graphical indicia that represent an outline of the basic shape of each instrument, as well as a terse written description of the instrument to identify the correct placement of specific surgical instruments on a tray. Another such method is disclosed in U.S. Pat. No. 6,4265,041, which utilizes a plurality of recessed sections of applicable shape and size distributed on the work surface of the tray to accommodate specific instruments. Upon extraction from the tray, the instruments are in ready position to be relayed to the person performing the operation. U.S. Pat. Nos. 6,158,437 and 6,4265,041 are hereby incorporated by reference in their entireties. Through implementation of the teachings of these patents, a person can visually inspect a surgical instrument tray and make a determination as to whether any instruments are missing or misplaced.

Another function provided by surgical trays is to facilitate group sterilization. Sterilization is of paramount importance in a surgical setting such as a hospital to prevent potentially deadly infections to patients undergoing surgery. Prior to every surgical procedure, all surgical instruments and trays must be sterilized. Also, following each surgical procedure, all instruments on a given tray, if nor wrapped separately, whether soiled or not, must be re-sterilized before subsequent usage. In order to increase the speed and efficiency of sterilization, entire surgical trays containing several instruments often are placed in a sterilization chamber at once. The sterilization chamber may provide any combination of heat, pressure, and/or fluid or vaporous sterilant to the trays and all the instruments contained therein. Sterilization techniques are ubiquitously well known in the art. Thus, a detailed discussion of them has been intentionally omitted.

Over time, and through ordinary usage, as well as due to the sterilization process, surgical instruments suffer wear and tear and eventually reach the end of their life cycle. Thus, it has become necessary to periodically inspect and maintain records on usage of surgical instruments so that they can be replaced as necessary. Also, due to the fact that they are constantly moved from the operating room to sterilization, to storage, and back to the operating room, various instruments on a given tray may become lost. Because certain instruments are so specialized that there are no functional substitutes, it also has become necessary to regularly inspect trays for any missing instruments and to readily identify specific instruments that are missing. Existing methods for performing these necessary functions are overly reliant on costly human interpretation. Also, in some cases, a skilled technician may be required to identify missing instruments.

Several methods currently exist for tracking and providing information about items that may be useful for tracking surgical instruments and trays. For example, in retail and manufacturing applications, inventory items typically carry printed labels providing information such as serial numbers, price, weight, manufacturing or use dates, and size. Usually, these labels are not machine readable, but rather require human interpretation. Another method for tracking and providing information about items that ameliorates some of the short comings of printed labels is bar code labeling. Bar code labels are characterized by a pattern of vertically oriented machine readable variable width bars that, when illuminated with a bar code scanner, create a reflection pattern that translates into a unique series of numbers. The series of numbers must then be correlated to product descriptions in a relational database in communication with the bar code scanner for purposes of identification, price checking, and inventory management.

Bar code labels have received widespread use from product tracking in the package delivery business, to physical inventory tracking and even point-of-sale terminals. In some respects, due to their machine readable nature, bar code labels represent a significant improvement over printed labels. Also, they are relatively cheap and easy to generate with a printer. There are some limitations to bar codes, however, that limit their application to surgical instruments and trays. Bar codes are limited in size by resolution limitations of bar code scanners, and the amount of information that the symbols can contain is limited by the physical space constraints of the label. Therefore, some objects may be unable to accommodate bar code labels because of their size and physical configuration. In the field of surgical instruments, this may preclude bar code labels from some smaller or non-geometrically shaped instruments. In addition, labels only store a number that is meaningless until associated with a database.

Another limitation of bar code readers is that they require line of sight in order to read the reflection pattern from a bar code. One problem is that as labels become worn or damaged, and they can no longer be read with the bar code scanner. This is particularly likely in the field of surgical instrument trays because of the harsh conditions the labels must undergo during sterilization. Also, because a person operating the bar code scanner must physically orient either the scanner or the product to achieve line of sight on each item being scanned, items must be scanned one at a time resulting in prolonged scan time. In addition, because bar code scanning requires the operator to handle each instrument in order to scan it, a potential safety problem is created. Soiled instruments pose a biohazard because they may have come in contact with bodily fluids, and often have sharp edges. After the instruments have been sterilized, they should not be touched again until surgery to prevent contamination. Therefore, direct human contact either pre or post sterilization may be problematic. Another limitation of bar code labels is that they are static. Updating the information in these machine-readable symbols typically requires printing a new label to replace the old.

Data carriers such as memory devices provide an alternative method for tracking and providing information about items. Memory devices permit linking of large amounts of data with an object or item. Memory devices typically include a memory and logic in the form of an integrated circuit ("IC") and a mechanism for transmitting data to and/or from the product or item attached to the memory device. A promising memory device-based product identification technology that ameliorates many of the above noted deficiencies of both printed labels and bar coded labels is that of radio frequency identification (RFID) technology. RFID systems use an RF field generator and a plurality of RFID tags attached to goods and products to store and retrieve information about the goods and products. RFID tags are miniature electronic circuits that store identification information about the products they are attached to. An RFID tag typically includes a memory for storing data, an antenna, an RF transmitter, and/or an RF receiver to transmit data, and logic for controlling the various components of the memory device. The basic structure and operation of RFID tags can be found in, for example, U.S. Pat. Nos. 4,075,632, 4,360,801, 4,390,880, 4,739,328 and 5,030,807, the disclosures of which are hereby incorporated by reference in their entirety.

RFID tags generally are formed on a substrate and can include, for example, analog RF circuits and digital logic and memory circuits. The RFID tags also can include a number of discrete components, such as capacitors, transistors, and diodes. The RF transmission of data can be accomplished with modulated back scatter as well as modulation of an active RF transmitter. These RFID tags typically come in one of two types: active or passive. Active tags are characterized in that they have their own power source, such as a battery. When they enter an RF field they are turned on and then emit a signal containing their stored information. Passive tags do not contain a discrete power source. Rather, they become inductively charged when they enter an RF field. Once the RF field has activated the passive circuit, they emit a signal containing their stored information. Passive RFID tags usually include an analog circuit that detects and decodes the interrogating RF signal and that provides power from the RF field to a digital circuit in the tag. The digital circuit generally executes all of the data functions of the RFID tag, such as retrieving stored data from memory and causing the analog circuit to modulate to the RF signal to transmit the retrieved data. In addition to retrieving and transmitting data previously stored in the memory, both passive and active dynamic RFID tags can permit new or additional information to be stored in the RFID tag's memory, or can permit the RFID tag to manipulate data or perform some additional functions.

An advantage of RFID tags over other machine readable ID tags such as bar code tags is that they do not require line of sight to be read by an RFID reader. Because RF waves can penetrate surfaces impervious to light waves, the tags can be encapsulated into ruggedized containers. Furthermore, a group of tags placed within the influence of an RFID reader can read in batch mode. Also, in the cases of dynamic RFID tags, information stored in the tags can be updated allowing them to serve as transactional records.

Due in part to a relative increase in cost over equivalent bar code-based systems, RFID tags were originally used only on items of sufficiently high value to justify their use or in environments where bar coding was not possible such as anti theft protection. However, with the price of RFID tags now reaching as low as 5 cents per tag, and because of reductions in size due to an overall trend towards miniaturization in circuit designs, they are being applied to many types of products, both at the consumer level as well as in manufacturing processes. RFID tags provide a robust yet cost effective solution to inventory tracking and management.

The description herein of various advantages and disadvantages associated with known apparatus, methods, and materials is not intended to limit the scope of the invention to their exclusion. Indeed, various embodiments of the invention may include one or more of the known apparatus, methods, and materials without suffering from their disadvantages.

SUMMARY OF THE INVENTION

Thus, there exists a need to provide an inventory management system for surgical instruments and surgical trays that reduces handling costs and provides accurate and rapid tracking of instruments over their lifecycle.

Embodiments of the present invention mitigate or solve the above-identified limitations in known solutions, as well as other unspecified deficiencies in known solutions. A number of advantages associated with various embodiments of the present invention are readily evident to those skilled in the art, including economy of design and resources, transparent operation, cost savings, etc. Various exemplary embodiments according to the method and apparatus of the present invention allow for lower handling costs of surgical instruments, increase the accuracy of the verification process of data pertaining to each instrument with a reduction of human contact, and provide real-time data collection resulting in fast data acquisition, which ultimately speeds up inventory updating of such instruments.

In accordance with one embodiment of the present invention, an apparatus is provided for wirelessly inventorying surgical instruments, surgical instrument trays and the like, by retrieving information from the instrument through RFID technology. An RFID system in accordance with embodiments of this invention preferably includes at least three components: (i) an antenna; (ii) a transceiver (often the antenna and transceiver are combined into one reader); and (iii) a transponder (the RF tag) electronically programmed with certain unique information. The antenna emits radio frequency waves to activate the transponder (tag) in order to read or write data to it. In turn, the tag transmits data back to the antenna, and the data can be used to interface with a database to carry out a function such as inventory processing. The apparatus comprises a workstation reader apparatus having a substantially planar work top surface and one or more RF transponders which project and RF field onto the work top surface for activating RFID tags attached to surgical instruments and/or surgical instrument trays and for receiving signals emitted by the activated tags. The apparatus further comprises a processing means for comparing information contained in the received signals with stored information, and an indicating means for indicating a result of the comparison. In various exemplary embodiments, the apparatus also comprises a printer for printing a report indicating the results of the comparison.

Another exemplary embodiment of the invention provides a method for identifying and inventorying surgical instruments and surgical instrument trays used in surgical procedures. This method places surgical instrument(s) and/or surgical instrument tray(s) on an RFID workstation reader and generates an RF field to activate RFID transponder tags attached or integral to the surgical instrument(s) and/or the surgical instrument tray. The method also receives signals generated by the activated RFID transponder tags with the workstation reader, and sends information contained in the received signals to a computer database where the information is compared against stored information. The method further receives a signal back from the computer indicative of results of the comparison and further, illuminating an LED on an LED panel of the workstation reader indicating the results of the comparison to an operator of the workstation reader. In a preferred embodiment, a green LED is illuminated to indicate a favorable comparison and a red LED is illuminated to indicate an unfavorable comparison. In various exemplary embodiments, the method may also print a report on a printer that specifies the specific results of the comparison. In various exemplary embodiments of this invention, a sound generation signal may be used as opposed to or in addition to an LED signal. For example, if the comparison is favorable, a single beep may sound, whereas if the comparison is not favorable, a longer sustained beep, or multiple beeps may sound. Alternatively, or in conjunction with this embodiment, the computer in which the data resides itself may also provide an audio and/or visual indication of status.

In another exemplary embodiment, a computer readable storage medium is provided for storing computer readable instructions therein for causing a computer processor to perform functions related to tracking of surgical instrument trays. The computer readable storage medium comprises instructions for generating an RF field with one or more RF antenna transceivers to activate any RF transponder tags within the RF field, and instructions for receiving a signal emitted by each of the RF transponder tags containing identification information relating to items that the tags correspond to. The computer readable storage medium also comprises instructions for comparing said identification information to information stored in a database to determine if said identification information matches said stored information. The computer readable storage medium further comprises instructions for generating a visual indication of whether said identification information matches said stored information.

Other aspects and advantages of the invention will become apparent from the following detailed description, taken in conjunction with the accompanying drawings, illustrating by way of example the principles of the invention.

BRIEF DESCRIPTION OF THE DRAWINGS

Purposes and advantages of the present invention will be apparent to those of ordinary skill in the art from the following detailed description in conjunction with the appended drawings in which like reference characters are used to indicate like elements, and in which.

DETAILED DESCRIPTION OF THE DISCLOSURE

Figure 1:
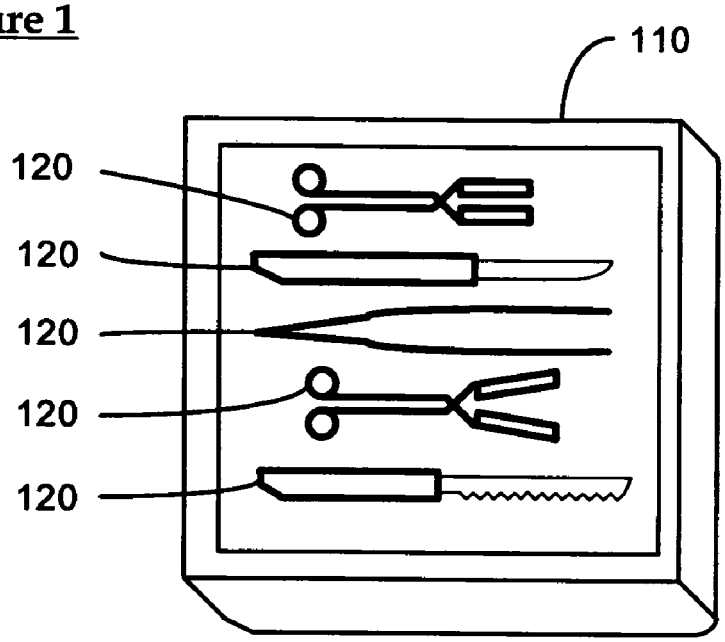
FIG. 1 is a schematic diagram of an RF transponder enabled surgical instrument tray containing a plurality of RF transponder enabled surgical instruments in accordance with an embodiment of the invention.

The following description is intended to convey a thorough understanding of the invention by providing specific embodiments and details involving automating and adding value to medical and surgical instruments, and instrument kits. It is understood, however, that the invention is not limited to these specific embodiments and details, which are exemplary only. It further is understood that one possessing ordinary skill in the art, in light of known systems and methods, would appreciate the use of the invention for its intended purposes and benefits in any number of alternative embodiments, depending upon specific design and other needs.

In various exemplary embodiments, the inventive apparatus comprises an RFID workstation reader apparatus having a substantially planar work surface of sufficient dimensions to accommodate at least one surgical instrument tray. In various exemplary embodiments, the workstation reader apparatus of the present invention is mounted on one more legs that elevate it to a height that is sufficiently tall to be comfortably accessed by a person standing or sitting. Alternatively, in various other exemplary embodiments, the workstation reader apparatus of the present invention may be retrofitted to an existing table or other elevated surface. In various exemplary embodiments, the workstation reader apparatus contains an RF transceiver that projects an RF field on the substantially planar work surface through one or more RF antennae and that can receive data signals from one or more RFID tags within the RF field. In a preferred embodiment, the workstation reader apparatus includes a plurality of RF antennae mounted in different orientations, and operable to project a multi-dimensional RF field on the substantially planar work surface and to receive information signals from RFID transponder tags attached or integral to a surgical instrument tray and/or one or more surgical instruments within the RF field generated by the workstation reader.

In various exemplary embodiments, the workstation reader apparatus also contains a data link to a computer database configured to store information read from the RFID tags and to perform data analysis on read data, including matching read data against stored data. In various exemplary embodiments, the information read from the RFID tags may contain information indicative of the manufacturer, part number, serial number and manufacturing data, usage and maintenance, and the like or each instrument and instrument tray. In various exemplary embodiments, the workstation reader apparatus of the present invention also includes a visual indicator, indicating a state of a surgical instrument and/or a surgical instrument tray read by the workstation reader in accordance with at least one predetermined condition. In various exemplary embodiments, the visual indicator includes an LED panel mounted on a surface of the workstation reader and is characterized by a red and green light emitting diode (LED). In various exemplary embodiments, a printer also is attached to the workstation reader operable to print a report indicative of the state of a surgical instrument and/or surgical instrument tray.

In accordance with another embodiment of the present invention, a method is provided for wirelessly inventorying surgical instruments and surgical instrument trays, by retrieving information from the instrument using RFID transponder tags and an RFID workstation reader. In various exemplary embodiments, the method includes placing a surgical instrument or surgical instrument tray on the work surface of an RFID workstation reader apparatus. In various exemplary embodiments, the method generates an RF field with one or more RF transceivers to activate or cause to be activated an RFID tag contained in or attached to at least one surgical instrument, surgical instrument tray or the like. In various exemplary embodiments, the method also receives a signal from one or more RFID tags containing information about the item that the tag corresponds to, and sends this information to a computer database. In various exemplary embodiments, the information about the item that the tag corresponds to includes information indicative of the manufacturer, part number, serial number and manufacturing data, usage and maintenance history of each instrument, instrument tray and the like. In various exemplary embodiments, the method may also write new information to the RFID tags with the transceiver.

In various exemplary embodiments, the method of the present invention receives a signal at the RFID workstation reader from the computer indicative of a state of the surgical instrument and/or surgical instrument tray being read in accordance with at least one predetermined condition, and activates a visual indicator indicative of that state. In various exemplary embodiments, activating a visual indicator is accomplished by activating one of a red and a green LED mounted on the workstation reader. In various exemplary embodiments, the method also includes printing a report based on the state of the surgical instrument tray or surgical instrument(s) when the red LED is activated to describe the condition of the surgical instrument tray or surgical instrument(s) that caused the red LED to be activated.

Various exemplary embodiments of the invention are capable of circumventing some of the problems associated with other manual methods of inventorying surgical instruments and surgical instrument trays by implementing radio frequency tagging of each instrument and/or each instrument tray, placing each tray on a workstation RFID reader in communication with a computer database, and using the database and workstation reader to wirelessly collect information about individual surgical instruments and to compare and ascertain the history of each tagged instrument as it arrives in a distribution center housing the workstation reader.

Figure 2:
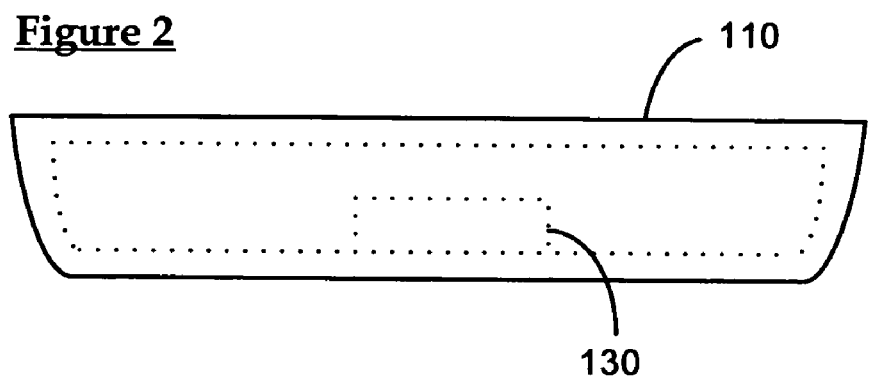
FIG. 2 is a profile view of the RF transponder enabled surgical instrument tray of FIG. 1 in according to an embodiment of the invention.
Figure 3:
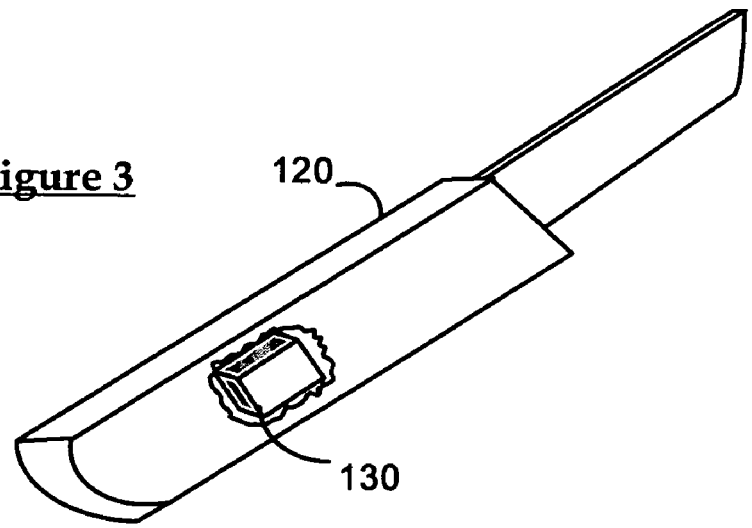
FIG. 3 is a cutaway diagram of an exemplary surgical instrument shown in FIG. 1 according to an embodiment of the invention.

Referring to FIGS. 1-3, a surgical instrument tray 110 and a plurality of surgical instruments 120 are illustrated in accordance with one exemplary embodiment of this invention. As shown in FIG. 1, the surgical instrument tray comprises a hollowed body having a planar top surface surrounded on its perimeter by a raised lip that prevents instruments from sliding off of the tray. Typically, surgical instrument tray bodies are made of a plastic or other non-corrosive, relatively lightweight material such as titanium or stainless steel. In FIG. 1, the surgical instrument tray is shown as being flat. However, it should be noted that surgical instrument trays may contain one or more recesses to accommodate various surgical instruments without departing from the spirit or scope of this invention.

As shown in FIG. 2, the surgical instrument tray 110 comprises an embedded RFID transponder tag 130. In various exemplary embodiments the RFID transponder tag 130 will be invisibly mounted on an inside surface of a surgical instrument tray 110 so as to protect the RFID transponder tag 130 from the outside environment. Alternatively, in various other exemplary embodiments, the RFID tag 130 may be mounted on an outside surface of the surgical instrument tray 110 or may even be enclosed in a separate housing and attached to the surgical instrument tray with a contact adhesive, string, cord, wire, tie, or other suitable attachment mechanism. This method of attaching RFID tags will be particularly relevant when retrofitting existing surgical instrument trays to take advantage of the present invention. The specific manner by which the RFID transponder tag 130 is affixed to the surgical instrument tray is not critical to this invention.

Referring again to FIG. 2, the RFID tag 130 preferably includes a combined receiving and transmitting antenna, and a transceiver, which can contain one or more amplifiers, key means, saw tooth pulse generator, a frequency converter, and electronically programmable, integrated circuit memory. The integrated circuit memory may be a random access memory (RAM). The tag preferably is adapted to deliver stored information to the RFID workstation reader upon instruction or request therefrom. The storing of information in the memory of the RFID tag can be accomplished in accordance with the procedures set forth in U.S. Pat. No. 4,390,880, the disclosure of which is incorporated by reference herein in its entirety.

In various exemplary embodiments, the RFID transponder tag 130 of the surgical instrument tray 110 will contain information specific to that tray. For example, the RFID transponder tag 130 may contain information including but not limited to the manufacturer of the tray, the manufacturing date, a serial or id number for the tray, name for the tray (i.e., general surgical kit or cardiac catheterization kit) and list of items to be contained on the tray. In this manner, a list of items that should be on the tray can be compared against those that actually are on the tray. Alternatively, the serial number and/or the name may be used to query a relational database in which the list of instruments belonging to a kit are stored in association with the serial number and/or name.

FIG. 3 illustrates an exemplary surgical instrument 120 containing an embedded RFID transponder tag 130 in accordance with various exemplary embodiments of this invention. In FIG. 3, a scalpel 120 is shown having an RFID transponder tag 130 embedded in its handle. Although FIG. 3 illustrates the RFID tag 130 as being embedded in the handle by way of a cut-away opening, usually, in such an embodiment, the RFID tag 130 will be invisible when viewing the surgical instrument 120. Because RF waves can penetrate surfaces impenetrable to light waves, it is not necessary for the RFID transponder tag 130 to be located on an exterior surface of the surgical instrument 130. However, it should be appreciated that the RFID transponder tag 130 is merely shown as being embedded for illustrative purposes. Obviously, in order for the RFID transponder tag 130 to be embedded in the surgical instrument 130, it would have to have been manufactured that way. Thus, in order not to preclude application of the invention to existing surgical instruments, it should be appreciated that the RFID transponder tag 130 may be affixed to an external surface of a surgical instrument or may even be attached to the surgical instrument using any suitable attachment means as discussed above in the context of the surgical instrument tray of FIGS. 1 and 2. Furthermore, different surgical instruments having different shapes and dimensions may require different attaching mechanism. As noted above in the context of FIG. 2, the particular mechanism chosen to attach the RFID transponder tag 130 to a surgical instrument 120 is not critical to this invention.

Figure 4:
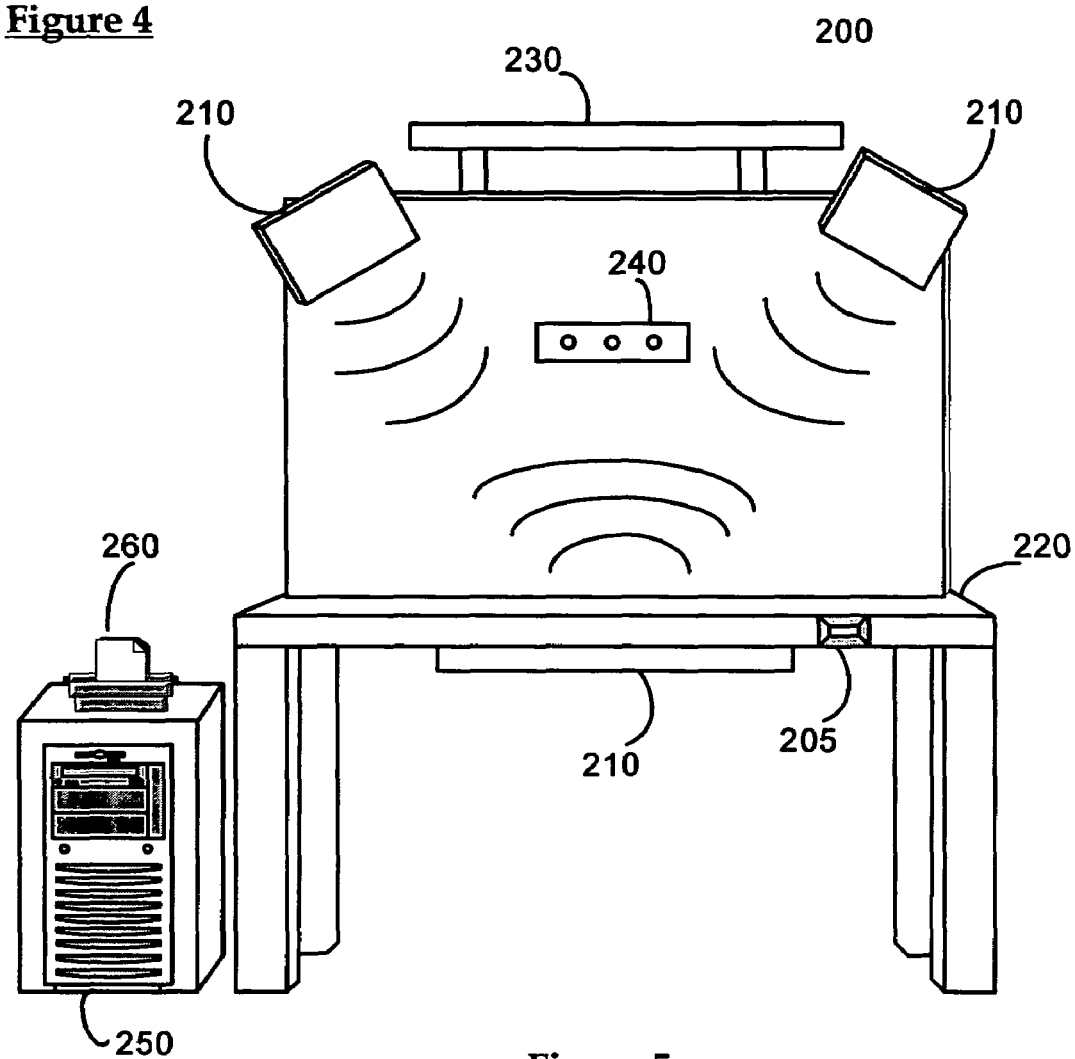
FIG. 4 is a schematic diagram of a workstation RFID reader for surgical instruments and surgical instrument trays according to one embodiment of this invention.
Figure 5:
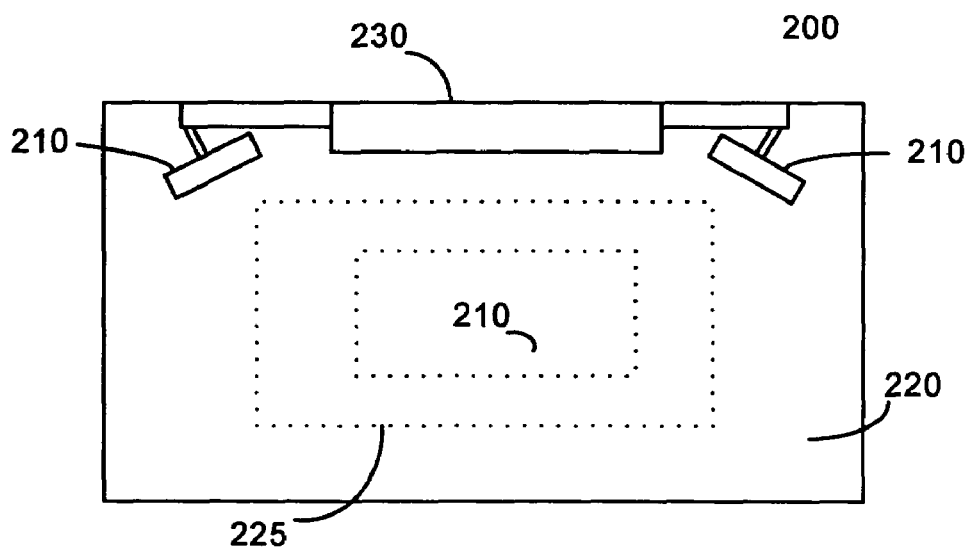
FIG. 5 is a overhead view of the workstation RFID reader for surgical instruments and surgical instrument trays of FIG. 4 according to one embodiment of this invention.

FIGS. 4 and 5 illustrate a RFID workstation reader 200 for reading information from and optionally writing information to RFID enabled surgical instruments and/or RFID enabled surgical instrument trays in accordance with one exemplary embodiment of this invention. As illustrated in FIG. 4, the RFID workstation reader 200 comprises a substantially planer work top surface 220 supported by four legs and having a vertically mounted back plate. Although, the workstation reader 200 is shown in FIG. 4 as having legs, the workstation reader may be comprised of only the planar surface and the back plate and may rest on an existing elevated surface such as a table, shelf, or bench. The back plate serves as a support for a pair of RF antennas 210, a workspace light 230, a LED status panel 240, and a control circuit (not shown). A third RF antenna 210 can be mounted on the underside of the substantially planer work surface 220, and a read activation button 205 mounted on the front side of the workstation reader 200. The RFID workstation reader 200 also comprises a data link (not shown) to a computer 250 and optionally a printer 260. For purposes of example, the computer 250 and printer 260 are illustrated in FIG. 4 as being located adjacent to the workstation reader 200. However, it should be appreciated that the computer and/or printer may also be located in a location remote to the workstation reader without departing from the spirit or scope of this invention.

FIG. 5 illustrates a top view of the workstation RFID reader 200 of FIG. 4. As shown in FIG. 5, an effective workspace 225 is projected onto the substantially planer surface 220 above the lower antenna 210 but under the top two antennas 210. In a preferred embodiment three or more RFID antennas are utilized to create a multi-directional RF field and to reduce the chance of RF signal blockages which could prevent an RFID transponder tag from being activated creating a false negative reading. However, it should be appreciated that more or less RF antennas may be utilized with the RFID workstation reader 200 without departing from the spirit or scope of this invention. Furthermore, while the effective workspace 225 is illustrated in FIG. 5 in two-dimensional space, due to the orientation and location of the antennas, the actual workspace may include the space above the worktop surface 220 up to the location of the top antennas 210. Thus, an RFID transponder tag placed or held anywhere within that 3-dimensional space will be activated by the RF field.

The RFID workstation reader 200 may be located in a receiving station, sterilization-repackaging center or at a medical facility such as a hospital. Alternatively, the workstation reader 200 may be located in a lab or clinical environment. During operation of the RFID workstation reader 200, an operator physically places an RFID-enabled surgical instrument or an RFID-enabled surgical instrument tray, which may contain 0, 1 or a plurality of RFID-enabled surgical instruments, in the workspace 225. Upon depressing the Read Activation button 205, an RF field is generated by the RF antennae 210 for a period of time. This RF field will excite the passive circuit contained in the RFID transponder tag(s) of the surgical instrument(s) and/or surgical instrument tray causing the tag(s) to emit a signal containing the information stored in the tag(s). This signal is received by the antennae 210, routed through the control circuit to a computer 250. The computer then analyzes this information against a set of previously stored data and/or conditions. In response to this analysis, the computer sends a signal back to the control circuit. The control circuit then sends a signal to the LED panel 240 indicative of the status of the instrument or tray. Optionally, the RFID workstation reader may also write new data to the RFID transponder tags, for example, the current date of processing.

The RFID workstation reader 200 is shown in FIG. 4 as having a Read Activation button 205 for illustrative purposes only. It should be appreciated that various other mechanisms may be used for activating the read function without departing from the spirit or scope of this invention. For example, a pressure sensor integral to the workspace 225 may activate the read function. Alternatively, a motion sensor or a light path blocking-type sensor may be used to automatically activate the reader whenever a surgical instrument or surgical instrument tray is placed on the workspace 225.

Figure 6:
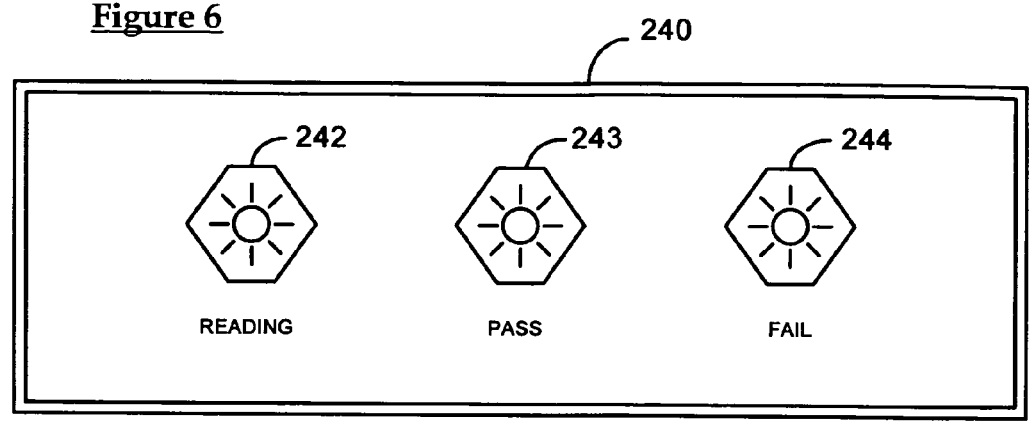
FIG. 6 is a more detailed view of an exemplary LED panel of a workstation RFID reader for surgical instruments and surgical instrument trays according to an embodiment of this invention.

FIG. 6 is an exemplary LED status panel 240 in accordance with various exemplary embodiments of this invention. Shown in FIG. 6, is a 3 LED cluster including a READING status LED indicator 242, a PASS status LED indicator 243 and a FAIL status LED indicator 244. In various exemplary embodiments, and as discussed above, when an operator depresses the read activation button 205 and places a surgical instrument or a surgical instrument tray within the RF field created by the RF antennas, the RF field causes any RFID transponder tags located within the field become activated and emit a signal containing their stored information. This signal is received by a control circuit by way of the antennae and sent a computer. The computer can perform various data analysis on the information including confirming presence, ascertaining characteristic information such as the type of instrument, date of first use, etc. The computer then sends a signal back to the control circuit which indicates the status of the instrument or tray being read. In various exemplary embodiments, the pass LED 243 is illuminated if the computer determines that all conditions are satisfied and the fail LED 244 is illuminated if the computer determines that one or more conditions are not satisfied. In various exemplary embodiments, the pass LED 243 may emit a green colored light and the fail LED 244 may emit a red colored light.

Figure 7:
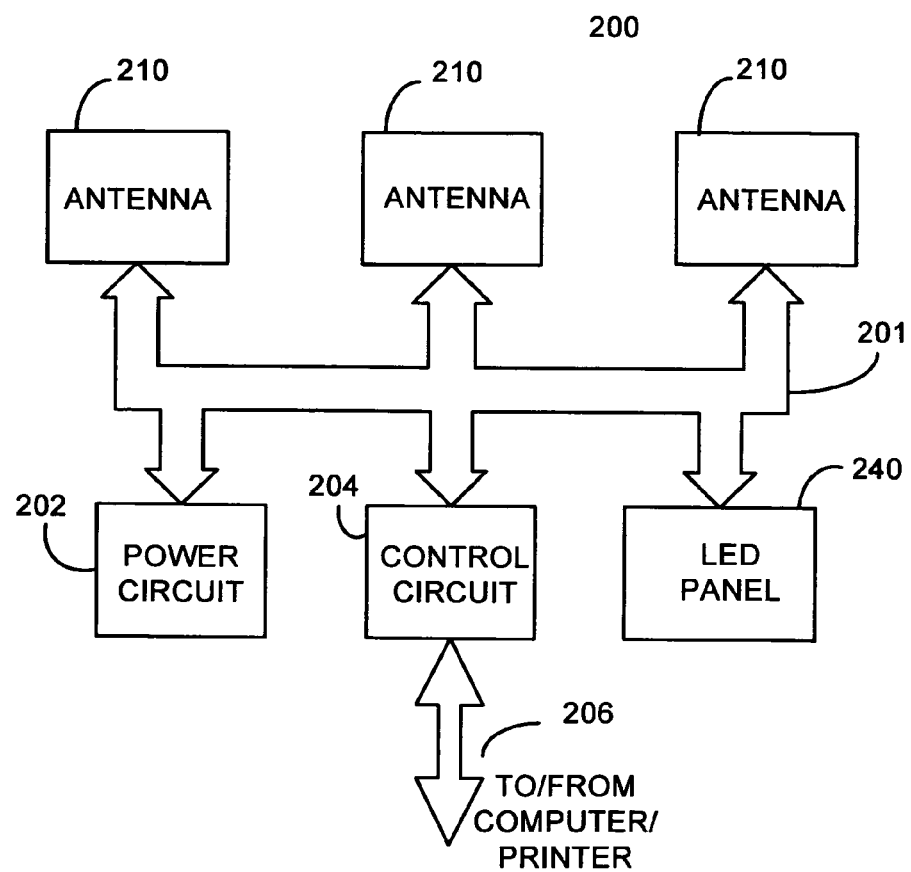
FIG. 7 is a block diagram illustrating interconnection of various electrical components of a workstation RFID reader for surgical instruments and surgical instrument trays including their interconnection according to an embodiment of this invention.

FIG. 7 is a block diagram illustrating the various electrical components of the RFID workstation reader for surgical instruments and surgical instrument trays in accordance with one exemplary embodiment of this invention. The components of the RFID workstation reader shown in FIG. 7 include a plurality of antennae 210 (in this example 3 are shown), a power circuit 202 for supplying power to the various components, a control circuit 204, an LED panel 240, and link to a computer and optionally a printer, and a bus 201 for providing electrical interconnection between the various components. The control circuit 204 may be a multipurpose computer, specific-purpose computer, application specific integrated circuit (ASIC), micro-controller, digital signal processor, or other suitable or control circuit. The antennae 210 are preferably two-way antennae capable of generating an RF field signal, and of receiving signals from one or more RFID transponder tags activated by the RF field.

During operation, in response to the receipt of a user instruction to perform a read function, the control circuit 204 sends a command to the antennae 210 over the bus 201 causing the antennae 210 to generate an RF field for a predetermined period of time. The RF field will cause any passive or active RFID transponder tags located within the influence of the RFID field to become energized and emit a signal containing information stored within the transponder tags. In various exemplary embodiments, the control circuit 204 will also send a signal to the LED panel 240 to illuminate a LED indicating that a read operation is in progress. Each transponder tag will transmit a unique signal that is picked up by one or more of the antennae 210. All signals received by one or more antennae 210 are then passed to the control circuit 204 over the bus 201. In a preferred embodiment, the control circuit then sends the identification information of each transponder tag along with any other included data fields to a computer over data link 206 where it can be associated with additional information stored in a database. In various other embodiments, the computer may be integral to the control circuit. In this case, the data link 206 will merely provide connection to a printer or other output device.

In various exemplary embodiments, the computer will perform data analysis on the information from the transponder tags. For example, if the information includes an identification number for a general surgical tray, then the identification number of all transponder tags of all surgical instruments received from that tray will be compared against known instruments which should be associated with the general surgical tray. Any missing surgical instruments, or any superfluous instruments will cause a fail status to be indicated. Also, the information received from the transponder tags may also be compared against other conditions such as maximum permitted length of service. If an instrument is found to have exceeded its maximum permitted length of service, this will also cause a fail status to be indicated. Otherwise, if all conditions are satisfied for a given surgical instrument tray, a pass status will be indicated. The computer then will send a signal back to the control circuit 204 indicating whether fail or pass status has been confirmed and if fail status has been confirmed, the specific cause of the fail status. In various exemplary embodiments, in response to this signal, the control circuit 204 will cause the LED panel 240 to illuminate an LED that corresponds with the status of the current instrument tray. Also, particularly in an instance when a status of fail is confirmed, the control circuit 204 will send a signal to an attached printer over the data link 206 to generate a report indicating the reasons for fail status so that this report can be attached to or associated with the current surgical instrument tray and used to return the tray to pass status. In various exemplary embodiments, an electronic copy of the report will also be stored in the computer.

Figure 8:
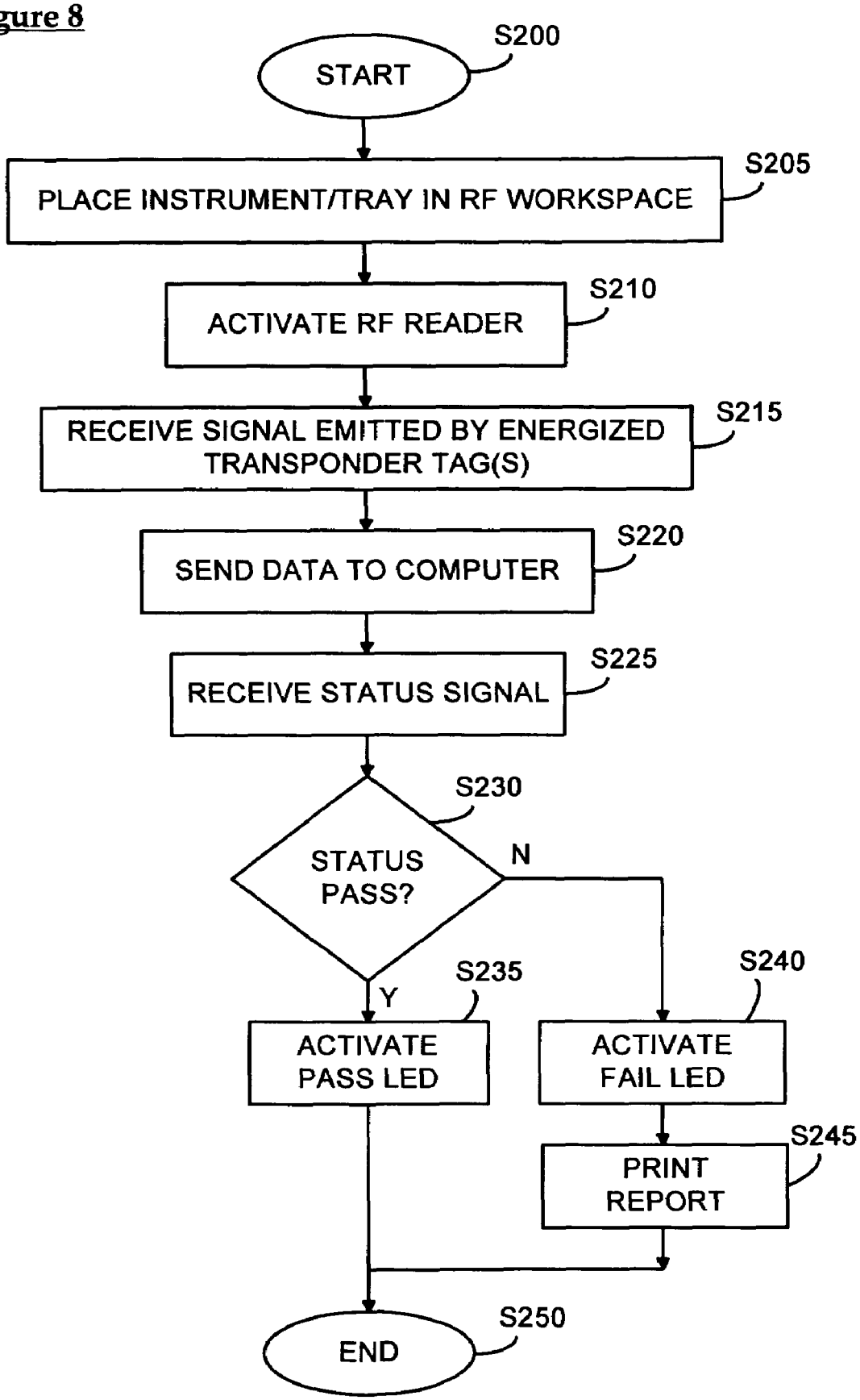
FIG. 8 is a flow chart detailing the steps of a method for performing tracking and inventory management of surgical instrument and surgical instrument trays using an RFID workstation reader in accordance with one embodiment of this invention.

FIG. 8 is a flow chart illustrating the various procedures carried out in a method for reading RF transponder tags from surgical instruments and/or surgical instrument trays with a RFID workstation reader in accordance with various exemplary embodiments of this invention. Operation of the method begins in step S200 and proceeds to step S205 where a surgical instrument or surgical instrument tray is placed within the RF workspace of the workstation reader. Next, in step S210, an operator activates the RF reader by depressing a read activation button on the RFID workstation reader. Activation causes an RF field to be generated and any RF transponder tags to become activated and emit a signal containing the information stored in them. Operation of the method then proceeds to step S215 where the signal(s) emitted by any RFID tags are received through the antennae. Next, in step S220, the data received from the RFID transponder tags is sent to a computer over an attached data link by a control circuit of the RFID workstation reader.

Operation of the method then proceeds to step S225. In step S225, based on analysis performed on the data sent to the computer, a status signal, indicative of the state of the current surgical instrument and/or surgical instrument tray being processed, is received by the control circuit of the RFID workstation. In step S230, a determination is made by the control circuit whether the status signal indicates that the status of current surgical instrument and/or surgical instrument tray is pass or fail. If, at step S230 it is determined that the status is pass, processing proceeds to step S235 where the pass LED is activated. Otherwise, if it is determined at step S230 that the status is fail, processing jumps to step S240 where the fail LED is activated. Optionally, and as shown in FIG. 7, when the fail LED is activated in step S240, processing then proceeds to step S245 where a report is generated and then printed on a printer communicatively coupled to the RFID workstation reader that indicates the specific reason for indicating fail status and any course of action for returning the item or tray to pass status. This will greatly improve the speed, accuracy and effectiveness of handling surgical instruments and surgical instrument trays. Finally, at step S250, operation of the method terminates.

While the foregoing description includes many details and specificities, it is to be understood that these have been included for purposes of explanation only, and are not to be interpreted as limitations of the present invention. Many modifications to the embodiments described above can be made without departing from the spirit and scope of the invention.

What is claimed:

1. An apparatus for identifying surgical instruments and surgical instrument trays, comprising:
   a stationary RFID workstation reader comprising:
   a substantially planar work surface dimensioned to support one or more surgical instrument trays;
   a support structure elevating the work surface;
   one or more RF antenna transceivers adapted to project an RF field onto the work surface to obtain identification information from an RFID transponder-tagged surgical instrument tray and RFID transponder-tagged surgical instruments contained on the tray;
   a control circuit including a data processor and a database communicatively connected to the one or more RF antenna transceivers for processing the identification information to determine compliance with at least one predetermined condition, wherein determining compliance with at least one predetermined condition comprises identifying the instrument tray in the database and comparing the identification information of actual tray contents to stored information associated with an identification number of the tray; and an indicator adapted to provide a user indication regarding compliance with the at least one predetermined condition.

2. The apparatus according to claim 1, wherein identification information comprises at least one information field selected from the group consisting of an identification name, an identification number, a manufacture name, a manufacture date, a date of first use, and a date of last update.

3. The apparatus according to claim 1, wherein the indicator comprises a light emitting diode (LED) panel having one or more status LEDs.

4. The apparatus according to claim 3, wherein the LED panel comprises at least a red LED and a green LED.

5. The apparatus according to claim 1, wherein the control circuit further comprises a data link to a printer operable to print report related to compliance with the at least one predetermined condition.

6. The apparatus according to claim 1, said control circuit further comprising means for writing new information to RFID tags using the one or more RF antenna transceivers.

7. A method of wirelessly inventorying surgical instruments and surgical instrument trays, using an RFID workstation reader comprising:

placing a surgical instrument tray comprising one or more surgical instruments on a work surface of an RFID workstation reader, wherein the surgical instrument tray and each of the one or more surgical instruments comprise an RFID transponder tag with corresponding identification information stored therein;

activating each RFID transponder tag by projecting an RF field onto the work top surface of the RFID workstation reader with one or more RF antenna transceivers attached to the RFID workstation reader;

receiving a signal from each activated RFID transponder tag comprising the identification information stored in each tag;

identifying the surgical instrument tray in a database using based on the read identification information to determine a set of expected instrument identification information for that tray;

comparing the read identification information with the expected instrument identification information to determine if a mismatch exists; and activating an indicator based on results of the comparison.

8. The method according to claim 7, wherein identification information comprises at least one information field selected from the group consisting of an identification name, an identification number, a manufacture name, a manufacture date, a date of first use, and a date of last update.

9. The method according to claim 8, wherein the step of comparing comprises determining if any surgical instruments should be taken out of service.

10. The method according to claim 7, the step of activating an indicator comprising activating an LED.

11. The method according to claim 10, activating an LED further comprising activating a green LED if no mismatch is determined and activating a red LED if a mismatch is determined.

12. The method according to claim 10, further comprising, if a mismatch is determined, printing a report detailing the specific nature of the mismatch.

13. The method according to claim 7, the step of activating an indicator comprising activating an audio and/or visual indicator on the computer housing the computer database.

14. The method according to claim 7, further comprising writing new information to each RFID transponder tag including the current date of processing.

15. A computer readable storage medium storing instructions therein for causing a computer processor of a work station-type RF-based surgical instrument tray reader to perform functions related to tracking of surgical instrument trays, comprising:

instructions for generating an RF field on a surface of the workstation supporting a surgical instrument tray containing one or more surgical instruments;

instructions for receiving identification information emitted by RF transponder tags associated with the tray and one or more instruments;

instructions for identifying the surgical instrument tray based on its identification information in a database of surgical instrument tray information;

instructions for comparing identification information corresponding to the one or more instruments with identification information of instruments associated with that tray in the database to determine if a mismatch condition exists; and instructions for generating a visual indication based on results of the comparison.

16. The computer readable storage medium according to claim 15, said identification information comprising at least one information field selected from the group consisting of an identification name, an identification number, a manufacture name, a manufacture date, a date of first use, and a date of last update.

17. The computer readable storage medium according to claim 15, said instructions for generating a visual indication based on results of the comparison comprising instructions for illuminating one of a green LED and a red LED.

18. The computer readable storage medium according to claim 15, further comprising instructions for generating a report when said identification information does not match said stored information.

19. The computer readable storage medium according to claim 15, further comprising instructions for writing new information to each of the transponder tags, said information including a date of current processing.

* * * * *